(12) United States Patent
Liu et al.

(10) Patent No.: US 10,188,606 B2
(45) Date of Patent: Jan. 29, 2019

(54) EXPANSILE CROSSLINKED POLYMERSOME FOR PH-SENSITIVE DELIVERY OF ANTICANCER DRUGS

(71) Applicant: Mayo Foundation for Medical Education and Research, Rochester, MN (US)

(72) Inventors: Xifeng Liu, Rochester, MN (US); Michael J. Yaszemski, Rochester, MN (US); Lichun Lu, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/728,181

(22) Filed: Oct. 9, 2017

(65) Prior Publication Data

US 2018/0098939 A1 Apr. 12, 2018

Related U.S. Application Data

(60) Provisional application No. 62/405,642, filed on Oct. 7, 2016.

(51) Int. Cl.

| | | |
|---|---|---|
| *C07D 319/06* | (2006.01) | |
| *A61K 31/704* | (2006.01) | |
| *A61K 9/127* | (2006.01) | |
| *C08G 65/332* | (2006.01) | |
| *A61K 9/00* | (2006.01) | |
| *C08G 65/331* | (2006.01) | |
| *C08G 65/337* | (2006.01) | |

(52) U.S. Cl.
CPC .......... *A61K 9/1273* (2013.01); *A61K 9/0019* (2013.01); *A61K 31/704* (2013.01); *C07D 319/06* (2013.01); *C08G 65/332* (2013.01); *C08G 65/337* (2013.01); *C08G 65/3315* (2013.01); *C08G 65/3318* (2013.01); *C08G 65/3328* (2013.01)

(58) Field of Classification Search
CPC .. A61K 9/1273; A61K 31/704; C07D 319/06; C08G 65/3328
See application file for complete search history.

(56) References Cited

U.S. PATENT DOCUMENTS

2013/0331426 A1* 12/2013 Gao .................. A61K 47/6845
514/422

OTHER PUBLICATIONS

Griset et al., 131 J. Am.Chem. Soc. 2469-2471 (2009) (Year: 2009).*
Anajafi and Mallik., "Polymersome-based drug-delivery strategies for cancer therapeutics," Ther Deliv., 4(4):521-534, Apr. 2015.
Liu et al., "Expansible crosslinked polymersome for pH sensitive delivery of doxorubicin," Biomater Sci., 4(2):245-249, Feb. 2016.
Lyisan et al., "Multifunctional and Dual-Responsive Polymersome as Robus Nanocontainers: Design, Formation by Sequential Post-Conjugations, and pH-Controlled Drug Release," Chem Mater., 28(5):1513-1525, 2016.
Meng et al., "Intracellular drug release nanosystems," Materials Today., 15(10):436-442, Oct. 2012.
Meng et al., "pH-sensitive polymeric nanoparticles for tumor-targeting doxorubicin delivery: concept and recent advances," Nanomedicine (Lond)., 9(3):487-499, Mar. 2014.

* cited by examiner

*Primary Examiner* — Timothy R Rozof
(74) *Attorney, Agent, or Firm* — Fish & Richardson P.C.

(57) ABSTRACT

This disclosure relates to polymersomes comprising a cross-linked polymer and their use as drug delivery vehicles. Specifically, polymersomes comprising a polymer of Formula I:

wherein each R is independently $C_{1-6}$ alkyl; and n is an integer between 1 and 50.

20 Claims, 15 Drawing Sheets

|  | Empty micelle | | | DOX-loaded micelle | | |
| --- | --- | --- | --- | --- | --- | --- |
|  | Size (nm) | PDI | Zeta (mV) | Size (nm) | PDI | Zeta (mV) |
| Uncrosslinked | 101.6 ± 3.6 | 0.46 ± 0.03 | -2.4 ± 1.5 | 113.9 ± 4.6 | 0.44 ± 0.01 | -1.3 ± 0.5 |
| Crosslinked | 96.3 ± 2.4 | 0.42 ± 0.03 | -2.8 ± 1.1 | 103.5 ± 5.3 | 0.45 ± 0.06 | -1.3 ± 0.3 |

FIG. 4

EXPANSILE CROSSLINKED POLYMERSOME FOR PH-SENSITIVE DELIVERY OF ANTICANCER DRUGS

CROSS REFERENCE TO RELATED APPLICATIONS

This application claims priority to U.S. Provisional Application Ser. No. 62/405,642, filed Oct. 7, 2016, which is hereby incorporated by reference in its entirety.

TECHNICAL FIELD

This disclosure relates to polymersomes comprising a crosslinked polymer and their use as drug delivery vehicles.

BACKGROUND

Delivery of anticancer drugs in a carrier could minimize damage to healthy tissues, prolong drug circulation time, and selectively accumulate drugs in tumors through enhanced permeability and retention (EPR) effect. Various carrier systems such as liposomes, quantum dots, and self-assembled nanoparticles or vesicles, have been reported in recent years. Amphiphilic polymers containing hydrophobic and hydrophilic segments can be readily self-assembled into nano-sized vesicles in aqueous solution. As one type of important self-assembled vesicles, polymersomes with stabilized structures have special capabilities of encapsulating guest molecules into their empty core domains and thus possess great potential for drug delivery.

SUMMARY

Provided herein are polymers of Formula (I):

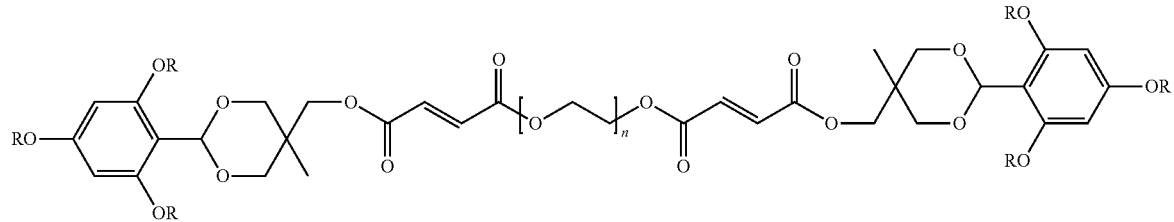

wherein each R is independently $C_{1-6}$ alkyl; and n is an integer between 1 and 50.

In some embodiments, n is an integer between 10 and 30. For example, n is an integer between 15 and 25. In some embodiments, n is 20.

In some embodiments, each R is methyl.

A non-limiting example of a polymer of Formula (I) includes:

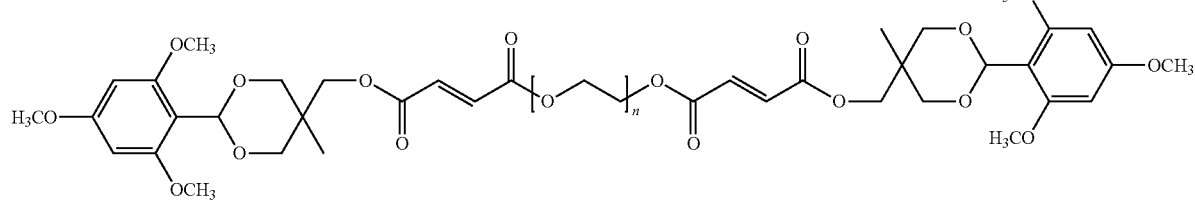

wherein n is as described above.

Also provided herein are polymersomes comprising a polymer of Formula (I) as described herein. In some embodiments, the polymer of Formula (I) is crosslinked.

In some embodiments, the polymersome further comprises a therapeutic agent. For example, the polymersome can further comprise a hydrophilic anticancer agent. Non-limiting examples of hydrophilic anticancer agents include doxorubicin, paclitaxel, 5-fluoroucacil, 6-mercaptopurine, cyclophosphamide, bleomycin, daunorubicin, epirubicin, methotrexate, vinblastine, homoharringtonine, actinomycin-D, mitocycin-c, and etoposide. In some embodiments, the hydrophilic anticancer agent is doxorubicin.

In some embodiments, the average diameter of the polymersomes is about 50 to about 150 nm. For example, the average diameter of the polymersomes is about 90 to about 120 nm.

Also provided herein are pharmaceutical compositions comprising a polymersome as described herein, and a pharmaceutically acceptable excipient.

Further provided herein is a method of treating cancer in a patient, the method comprising administering to the patient a therapeutically effective amount of a polymersome (e.g., a polymersome comprising a therapeutic agent, such as an anticancer agent) as described herein, or a pharmaceutical composition comprising the same.

Also provided herein is a method for administering a therapeutic agent to a patient in need thereof, the method comprising administering to the patient a polymersome (e.g., a polymersome comprising a therapeutic agent, such as an anticancer agent) as described herein, or a pharmaceutical composition comprising the same.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 depicts a table of particle size data for uncrosslinked and crosslinked PEG-Fu-DiTT polymersomes when both are empty or loaded with doxorubicin (DOX).

DETAILED DESCRIPTION

Figure 1:
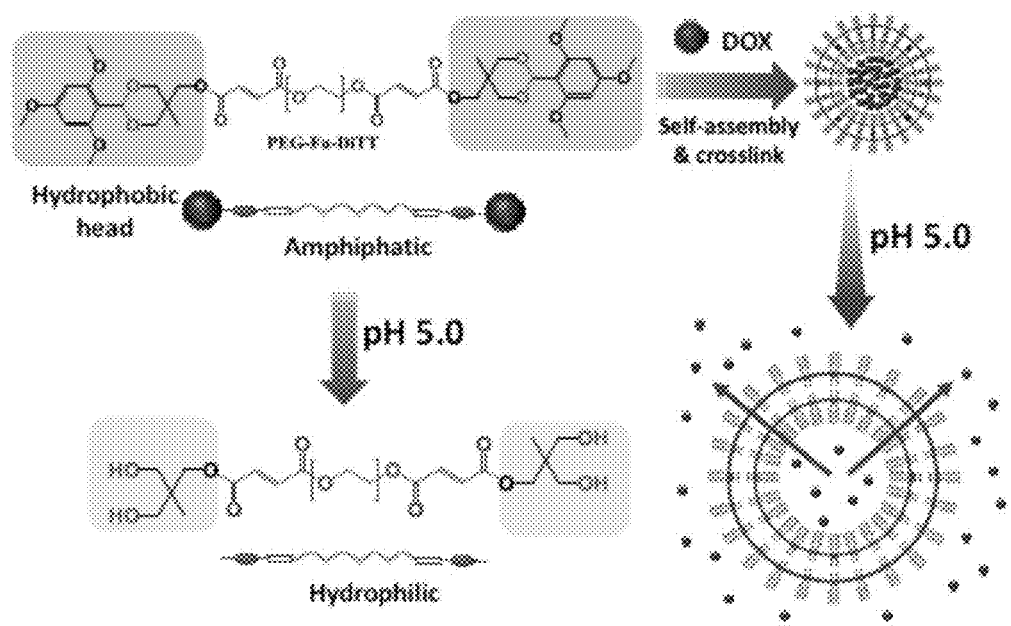
FIG. 1 depicts a schematic of self-assembly and crosslinking of PEG-Fu-DITT, and its subsequent release of doxorubicin.

As compared to liposomes, polymersomes are reported to have better mechanical strength, colloidal stability and lower drug leakage and thus are emerging as superior alternatives to liposomes. At the same time, all drug carrier systems, no matter if they are liposomes or polymersomes, are always associated with a practical challenges including low in vivo stability. Self-assembled particles have been reported to be easily eliminated from circulation due to in vivo disintegration. Hence, intensified covalent or noncovalent bonding that can resist the physiological destabilisation forces is highly desired for carriers aiming at sustained in vivo drug delivery. In recent years, several studies have incorporated cross-linkable properties to the carriers for improving stabilities. Crosslinking can occur in the hydrophilic shell, the hydrophobic core, or the core-shell interface, and various methods including photo irradiation and chemical reactions can be used to induce crosslinking.

In addition to in vivo stability, various stimuli, e.g., pH, temperature, light, enzyme and oxidation/reduction, can be used to trigger drug release from nanoparticles and polymersomes. To utilize these stimuli, a large variety of responsive bonds, such as acetal, orthoester and disulfide-linkers, can be designed and incorporated into the nanoparticle or polymersome. Upon the application of stimuli, the responsive bonds break or change properties and lead to the disassembly or expansion of the particles, resulting in the release of encapsulated drugs. Among these triggers, pH-responsive property is one of the most convenient and frequently selected characteristics in designing delivery system for tumor targeted drug delivery due to the lower pH profile in cancerous tissues and in lysosomes after cellular endocytosis. Provided herein are new crosslinked polymersome systems with superior in vivo stability and pH-sensitive drug release capabilities.

Polymers

The polymers provided herein are synthesized to have both a hydrophobic and hydrophilic segment that can be readily self-assembled into polymersomes and crosslinked. For example, provided herein is a polymer of Formula I:

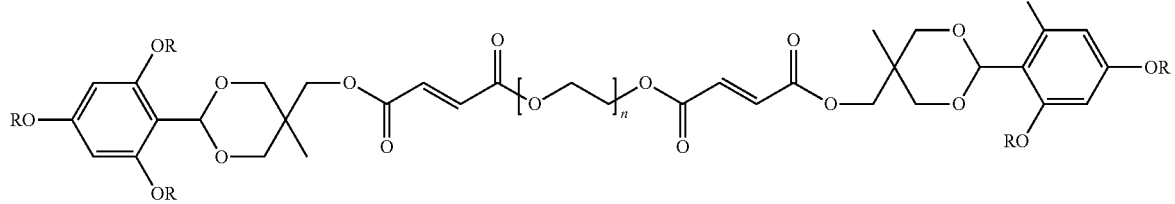

wherein each R is independently $C_{1-6}$ alkyl; and n is an integer between 1 and 50.

In some embodiments, n is an integer between 1 and 50 (e.g., between 1 and 40, between 1 and 30, between 1 and 25, between 1 and 20, between 1 and 15, between 1 and 10, between 10 and 50, between 15 and 50, between 20 and 50, between 25 and 50, between 30 and 50, between 35 and 50, between 40 and 50, between 10 and 30, between 15 and 25, between 20 and 40, between 10 and 40, and between 15 and 35. In some embodiments, n is an integer between 1 and 30. For example, n can be an integer between 15 and 20. In some embodiments, n can be 20.

In some embodiments, the polyethylene glycol moiety of the polymer of Formula I can have an average molecular weight of from about 200 to about 2000 g/mol. For example, the moiety:

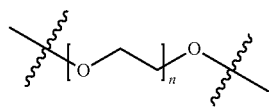

can have an average molecular weight of from about 200 to about 2000 g/mol. In some embodiments, the average molecular weight of the polyethylene glycol moiety of the polymer of Formula I is about 200 to about 1500 g/mol, about 200 to about 1200 g/mol, about 200 to about 1000 g/mol, about 200 to about 800 g/mol, about 200 to about 600 g/mol, about 200 to about 400 g/mol, about 300 to about 2000 g/mol, about 400 to about 2000 g/mol, about 600 to about 2000 g/mol, about 800 to about 2000 g/mol, about 1000 to about 2000 g/mol, about 1200 to about 2000 g/mol, about 400 to about 800 g/mol, about 300 to about 600 g/mol, about 600 to about 1200 g/mol, or about 600 to about 800 g/mol. In some embodiments, the average molecular weight of the polyethylene glycol moiety of the polymer of Formula I is about 200 g/mol, about 400 g/mol, about 600 g/mol, about 800 g/mol, about 1000 g/mol, about 1200 g/mol or about 2000 g/mol. In some embodiments, the average molecular weight of polyethylene glycol moiety of the polymer of Formula I is about 600 g/mol. In some embodiments, the polyethylene glycol moiety of the polymer of Formula I is PEG 200, PEG 400, PEG 600, PEG 800, PEG 1000, PEG 1500, or PEG 2000.

In some embodiments, each R is selected from methyl, ethyl, propyl, isopropyl, butyl, isobutyl, and tertbutyl. In some embodiments, all of the R groups are the same. For example, all of the R groups are methyl.

In some embodiments, the compound of Formula I is:

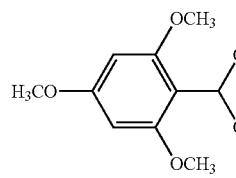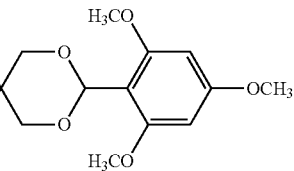

wherein n is as described above.

The polymers described herein can be prepared, for example, using the methods described in the Examples. In some embodiments, amphiphilic poly(ethylene glycol)-fumarate-di-2,4,6-trimethoxybezylidene-1,1,1-tris(hydroxymethyl) ethane (PEG-Fu-DiTT) polymer can be synthesized by linking a hydrophilic PEG chain (e.g., PEG 600) with hydrophobic 2,4,6-trimethoxybezylidene-1,1,1-tris(hydroxymethyl) ethane (TT) chains using fumarate chloride. TT monomers can be prepared from 1,1,1-tris(hydroxymethyl)ethane and 2,4,6-trimethoxybenzaldehyde in organic solvent (e.g., tetrahydrofuran (THF)). In some embodiments, the TT monomers are purified using a pH 8.0 buffer (e.g., Tris buffer).

Polymersomes

Provided herein are polymersome systems (e.g., crosslinked polymersome systems) with pH-sensitive drug release capability. One design feature for these polymersomes lies in the hydrophobic to hydrophilic transformation in response to low pH condition with subsequent size swelling. As noted above, the polymer chain is synthesized to have both hydrophobic and hydrophilic segments thus can be readily self-assembled into polymersomes. For example, a polymer of Formula I as provided herein. In some embodiments, the polymer is crosslinked.

Polymersomes can have an average diameter of about 50 nm to about 150 nm (e.g., about 50 nm to about 120 nm, about 50 nm to about 100 nm, about 50 nm to about 80 nm, about 50 nm to about 75 nm, about 60 nm to about 150 nm, about 75 nm to about 150 nm, about 80 nm to about 150 nm, about 100 nm to about 150 nm, about 120 nm to about 150 nm, about 60 nm to about 120 nm, about 80 nm to about 120 nm, about 75 nm to about 125 nm, about 90 nm to about 110 nm, about 90 nm to about 120 nm. In some embodiments, the polymersome has an average diameter of about 100 nm.

In some embodiments, the polymersome has a zeta-potential from about −0.5 mV to about −10 mV, or from about −1 mV to about −5 mV. In some embodiments, the zeta potential is from about −1.5 mV to about −2.5 mV, from about −1 mV to about −4 mV, or from about −2 mV to about −3 mV.

In some embodiments, the polymersomes present within a population, e.g., in a composition, can have substantially the same shape and/or size (i.e., they are "monodisperse"). For example, the polymersomes can have a distribution such that no more than about 5% or about 10% of the polymersomes have a diameter greater than about 10% greater than the average diameter of the particles, and in some cases, no more than about 8%, about 5%, about 3%, about 1%, about 0.3%, about 0.1%, about 0.03%, or about 0.01% have a diameter greater than about 10% greater than the average diameter of the polymersomes. In some embodiments, the diameter of no more than 25% of the polymersomes varies from the mean polymersomes diameter by more than 150%, 100%, 75%, 50%, 25%, 20%, 10%, or 5% of the mean polymersomes diameter. It is often desirable to produce a population of polymersomes that is relatively uniform in terms of size, shape, and/or composition so that most of the particles have similar properties. For example, at least 80%, at least 90%, or at least 95% of the polymersomes produced using the methods described herein can have a diameter or greatest dimension that falls within 5%, 10%, or 20% of the average diameter or greatest dimension.

The polymersomes (e.g., crosslinked polymersomes) provided herein are stable upon exposure to one or more of proteins, surfactants, and salt ions. For example, the polymersomes provided herein are stable in the presence of one or more of 10% fetal bovine serum (FBS), 5 mM sodium dodecyl sulfate (SDS), and 0.9% sodium chloride (NaCl) solution. Without being bound by any theory, it is believed that polymersomes gain enhanced stability after crosslinking of the inside chains.

Hollow polymersomes can be prepared as provided herein (see Examples). For example, hollow polymersomes can be prepared by self-assembly of poly(ethylene glycol)-fumarate-di-2,4,6-trimethoxybezylidene-1,1,1-tris(hydroxymethyl) ethane (PEG-Fu-DiTT) in 0.3% polyvinyl alcohol (PVA) aqueous solution. The amphiphilic PEG-Fu-DiTT polymer was synthesized by linking hydrophilic PEG chain with hydrophobic 2,4,6-trimethoxybezylidene-1,1,1-tris(hydroxymethyl) ethane (TT) chains using fumarate chloride. Polymers incorporated with fumarate segments are biocompatible and can be easily crosslinked through photo or chemical crosslinking. In some embodiments, the polymers are crosslinked using an ammonium persulfate (APS) and tetramethylethylenediamine (TEMED) solution.

In some embodiments, the polymersomes provided herein further comprise a therapeutic agent. For example, a hydrophilic therapeutic agent. In some embodiments, the hydrophilic therapeutic agent is a hydrophilic anticancer agent. For example, a hydrophilic anticancer agent can be selected from the group consisting of doxorubicin, paclitaxel, 5-fluorouracil, 6-mercaptopurine, cyclophosphamide, bleomycin, daunorubicin, epirubicin, methotrexate, vinblastine, homoharringtonine, actinomycin-D, mitocycin-c, and etoposide. In some embodiments, the hydrophilic anticancer agent is doxorubicin. Without being bound by any theory, it is believed that the hydrophilic therapeutic agents are encapsulated within the aqueous core of the polymersomes.

In some embodiments, the loading capacity of the polymersome with respect to the therapeutic agent is from about 1% to about 10% by weight of the total weight of drug-loaded polymersomes.

The polymersomes provided herein show excellent extracellular stability. Upon exposure to lower pH environments, the protecting group (i.e., 2,4,6-trimethoxybezylidene-1,1,1-tris(hydroxymethyl) ethane) on the polymer is cleaved, transforming the polymersomes into fully hydrophilic particles similar to hydrogels. As such, water can penetrate the polymersome dissolving the hydrophilic segments, which in turn causes swelling of the hydrogel particle, releasing the encapsulant (e.g., the therapeutic agent) in the core. In some of the embodiments provided herein, the advantages of this expansile polymersome system can include one or more of: 1) encapsulation of hydrophilic drugs such as doxorubicin (DOX); 2) good extracellular stability through internally crosslinking the polymersomes at the core-shell interface; 3) potent drug release upon exposure to the acidic environment in endosomes/lysosomes after endocytosis; and 4) an average size around 100 nm thus utilizing the EPR effect for selective accumulation in tumors.

Polymersomes (e.g., polymersomes including a therapeutic agent) can be formulated as a pharmaceutical composition in accordance with routine procedures. Pharmaceutical compositions can be administered by any route, including both oral and parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more doses separated in time, or as a constant or non-linear flow infusion. Thus, polymersomes can be formulated for any route of administration.

In some embodiments, a polymersome (e.g., a polymersome including a therapeutic agent) for intravenous administration are solutions in sterile isotonic aqueous buffer. Where necessary, the composition may also include a solubilizing agent, a stabilizing agent, and a local anesthetic such as lidocaine to ease pain at the site of the injection. Generally, the ingredients will be supplied either separately, e.g., in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions comprise the polymersome (e.g., a polymersome including a therapeutic agent) with any pharmaceutically acceptable ingredient, excipient, carrier, adjuvant or vehicle.

Pharmaceutically acceptable excipients, carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the polymersomes of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

In some embodiments, a polymersome (e.g, a polymersome including a therapeutic agent) is administered to the patient in the form of an injectable composition. The methods of administering a polymersome can include parenterally, meaning intravenously, intra-arterially, intrathecally, interstitially or intracavitarilly. Pharmaceutical compositions can be administered to mammals including humans in a manner similar to other diagnostic or therapeutic agents. The dosage to be administered, and the mode of administration will depend on a variety of factors including age, weight, sex, condition of the patient and genetic factors, and can be ultimately be decided by medical personnel.

Methods of Use

The polymersomes provided herein can be useful in the delivery of therapeutic agents. Accordingly, provided herein are methods of administering a therapeutic agent to a patient in need thereof, the method comprising administering a crosslinked polymersome comprising a therapeutic agent to the patient or a pharmaceutical composition comprising the same to the patient. For example, the crosslinked polymersomes provided herein can be useful for administering hydrophobic anticancer agents to a patient in need thereof. Accordingly, provided herein are methods for treating a cancer in a patient, the method comprising administration of a therapeutically effective amount of a polymersome comprising a therapeutic agent or a pharmaceutical composition comprising the same to the patient.

In some embodiments of any of the methods or uses described herein, the cancer is a solid tumor. In some embodiments of any of the methods or uses described herein, the cancer is lung cancer (e.g., small cell lung carcinoma or non-small cell lung carcinoma), papillary thyroid cancer, medullary thyroid cancer, differentiated thyroid cancer, recurrent thyroid cancer, refractory differentiated thyroid cancer, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

Definitions

Unless defined otherwise, all technical and scientific terms used herein have the same meaning as is commonly understood by one of ordinary skill in the art to which this disclosure belongs.

As used herein, the singular forms "a," "an," and "the" include plural referents unless the context clearly dictates otherwise.

As used herein, the term "about" means "approximately" (e.g., plus or minus approximately 10% of the indicated value).

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —$NH(C_{1-3}$ alkyl), and —$N(C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxyl) optionally substituted with one or more of halide, hydroxyl, —$NH_2$, —$NH(C_{1-3}$ alkyl), and —$N(C_{1-3}$ alkyl)$_2$; —OPO(OH)$_2$; a phosphonate [such as —PO(OH)$_2$ and —PO(OR')$_2$]; —OPO(OR')R"; —NRR'; —C(O)NRR'; —C(NR)NR'R"; —C(NR')R"; a cyano; a nitro; an azido; —SH; —S—R; —OSO$_2$(OR); a sulfonate [such as —SO$_2$(OH) and —SO$_2$(OR)]; —SO$_2$NR'R"; and —SO$_2$R; in which each occurrence of R, R' and R" are independently selected from H; —($C_{1-9}$ alkyl); $C_{6-10}$ aryl optionally substituted with from 1-3R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

The term "mammal" is used in its usual biological sense. Thus, it specifically includes humans, cattle, horses, monkeys, dogs, cats, mice, rats, cows, sheep, pigs, goats, and non-human primates, but also includes many other species.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

"Pharmaceutically acceptable" means that the polymersome can be administered to an animal without unacceptable adverse effects.

EXAMPLES

Materials and Methods
Characterizations
The chemical structures of synthesized polymers were confirmed using $^1$H NMR spectroscopy (300 MHz Varian NMR). Molecular weights of the obtained polymers were determined by Viscotek GPCMax/VE 2001 gel permeation chromatography (GPC) machine (Malvern Instruments, Inc.) using tetrahydrofuran as an eluent.

Example 1—Synthesis of 2,4,6-trimethoxybenzylidene-1,1,1-tris(hydroxymethyl)ethane (TT)

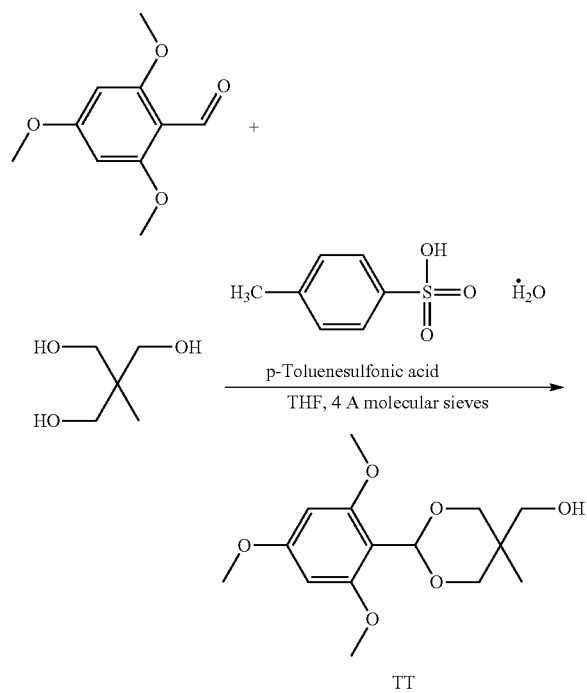

Figure 2A:
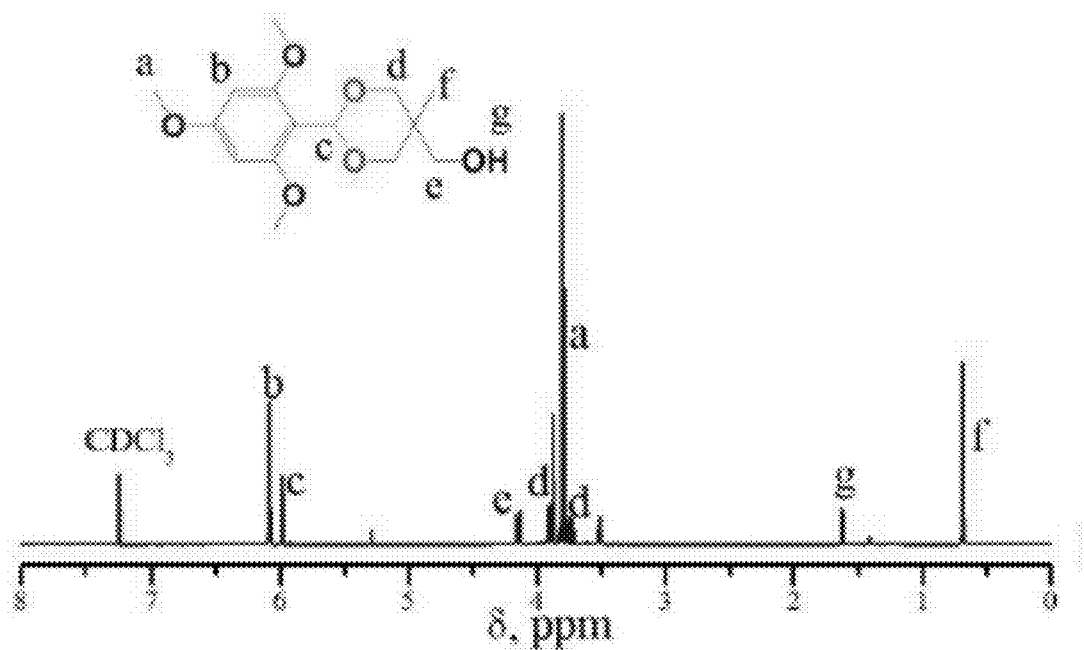
FIG. 2A shows an $^1$H NMR spectrum of 2,4,6-trimethoxybenzylidene-1,1,1-tris(hydroxymethyl)ethane.
Figure 2B:
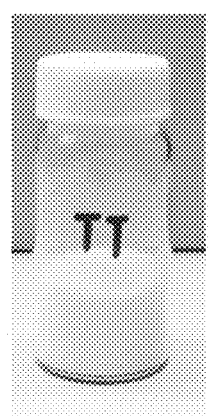
FIG. 2B provides a photograph of a sample of 2,4,6-trimethoxybenzylidene-1,1,1-tris(hydroxymethyl)ethane.

TT 6.7 g of 1,1,1-tris(hydroxymethyl)ethane (55.8 mmol) and 4.0 g of 2,4,6-trimethoxybenzaldehyde (20.5 mmol) were dissolved in 200 mL of tetrahydrofuran (THF) by means of vigorous stirring at room temperature. 50 g of 4 Å molecular sieves were then added as a desiccant and 0.473 g of p-toluenesulfonic acid (2.49 mmol) was added as a catalyst. The reaction mixture was stirred for 24 hours at ambient temperature. At the completion of the reaction, 8.0 mL of trimethylamine (TEA) was added to neutralize the acid. Afterwards, 200 mL of $CH_2Cl_2$ was added, and the mixture was filtered to remove the molecular sieves. The filtrate was collected and the solvents were removed by rotary evaporation. The resulting solid residue was re-dissolved in 200 mL of $CH_2Cl_2$ and washed with Tris buffer (100 mM, pH 8.0) three times to remove unreacted monomers, then dried over anhydrous magnesium sulfate. The $CH_2Cl_2$ solvent was then removed by rotary evaporation and the residue was washed with 200 mL of diethyl ether. The final product, 2,4,6-trimethoxybenzylidene-1,1,1-tris(hydroxymethyl)ethane, was dried under vacuum to give a light yellow solid. FIG. 2A is an $^1H$ NMR spectrum ($CDCl_3$) of the TT obtained. FIG. 2B depicts a photographic image of the TT. Yield: 4.9 g (80.3%).

Example 2—Synthesis of PEG-Fu-DiTT

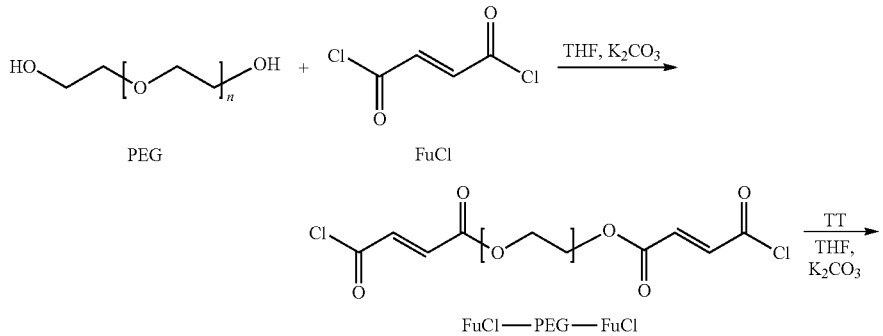

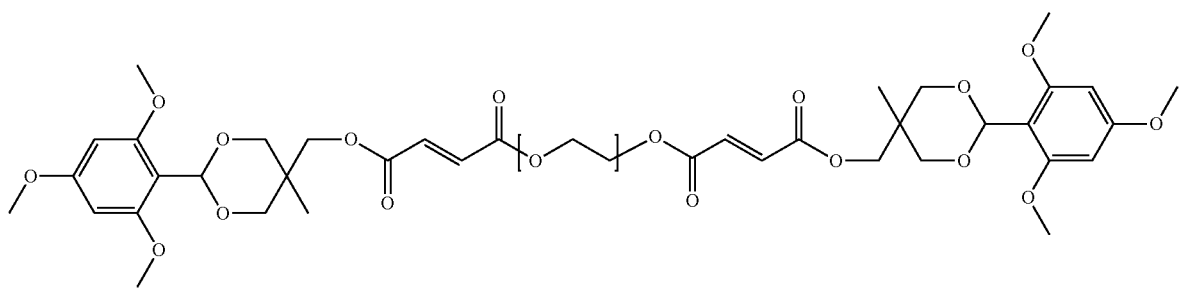

Figure 3A:
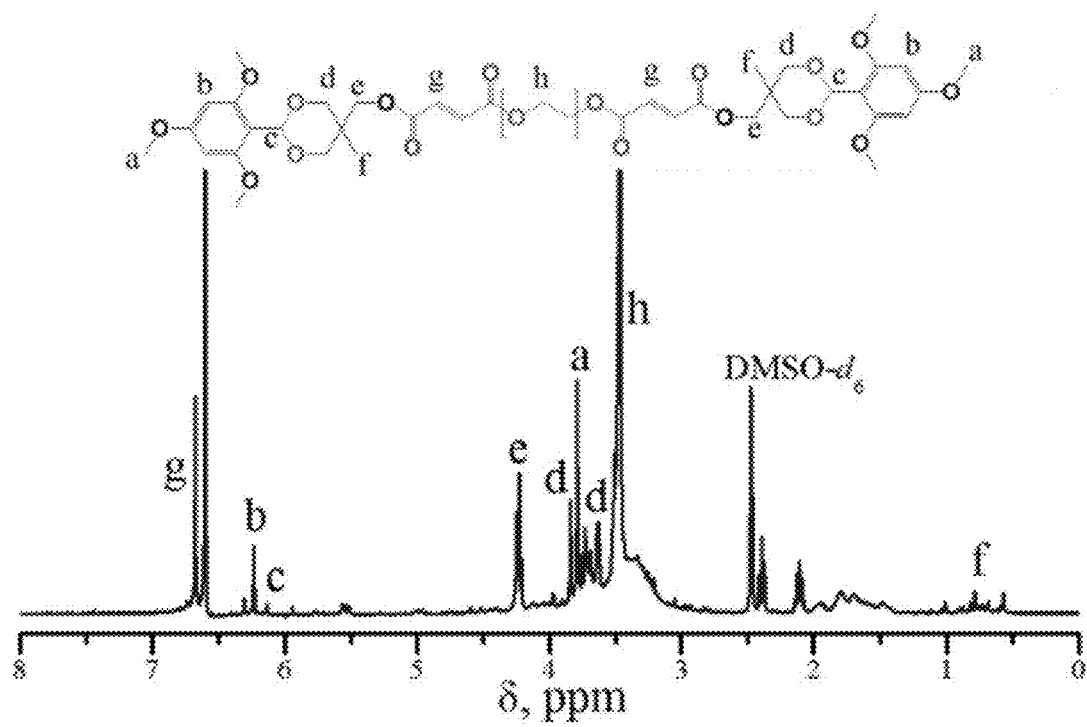
FIG. 3A shows an $^1$H NMR spectrum of PEG-Fu-DiTT.
Figure 3B:
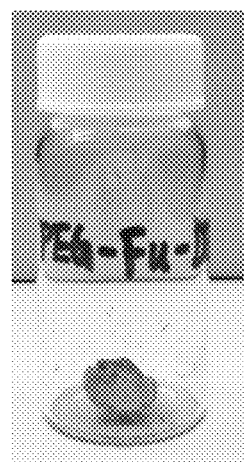
FIG. 3B provides a photograph of a sample of PEG-Fu-DiTT.

Excess fumaryl chloride (FuCl, 1 mL, density 1.4 g mL-1.9 mmol) was added to 10 mL of anhydrous $CH_2Cl_2$ in a 50 mL flask with 2 g potassium carbonate ($K_2CO_3$) as a proton scavenger. A solution of PEG 600 (0.2 g, 0.33 mmol, average Mn of 540 g mol$^{-1}$, M, =560 g mol$^{-1}$, and a PDI of 1.04) dissolved in 5 mL of anhydrous $CH_2Cl_2$ was then added dropwise to the flask while stirring. The reaction mixture was stirred overnight at room temperature and filtered to remove $K_2CO_3$ solids. The filtrate was concentrated under reduced pressure to remove $CH_2Cl_2$ solvent. Unreacted fumaryl chloride was then removed under vacuum to obtain FuCl-PEG-FuCl. To synthesize PEG-Fu-DiTT, 10 mL of THF was added to dissolve the FuCl-PEG-FuCl and the mixture was then transferred to another flask containing 0.2 g TT, 50 mL THF, and 2 g $K_2CO_3$. The mixture of FuCl-PEG-FuCl, TT, and $K_2CO_3$ was further stirred for 12 hours at room temperature and then filtered to remove $K_2CO_3$ solids. The filtrate was concentrated by rotary evaporation and the residue was precipitated in petroleum ether to obtain PEG-Fu-DiTT as a light brown solid. The PEG-Fu-DiTT was determined to have Mn=1380 g mol$^{-1}$, Mw=1710 g mol$^{-1}$, and a PDI of 1.24 as measured by GPC using the universal calibration method. FIG. 3A is a $^1$H NMR spectrum ($CDCl_3$) of the PEG-Fu-DiTT. FIG. 3B depicts a photographic image of the PEG-Fu-DiTT.

Example 3—Preparation and Characterization of Polymersomes 10 mg PEG-Fu-DiTT polymer was dissolved in 1 mL of THF while stirring. Then, 10 mL of a 0.3% solution of poly(vinyl alcohol) (PVA) solution was added slowly. The mixture was allowed to stir for 5 minutes, then residual THF was removed under reduced pressure. The final micelle concentration was 1.0 mg/mL. Crosslinked polymersomes were prepared by adding of 40 µL of 0.3 M ammonium persulfate (APS) and 40 µL of 0.3 M tetramethylethylenediamine (TEMED) to the above polymersome solution. Dynamic light scattering (DLS) was performed to determine the hydrodynamic sizes of formed micelles on a Zetasizer Nano ZS (Malvern Instruments). The size and morphology of micelles were further confirmed by Transmission electronic microscopy (TEM, JEOL 1400, Japan). To investigate the size changes of these uncrosslinked and crosslinked PEG-Fu-DiTT polymersomes, the solution pH was adjusted to 7.4 using phosphate buffer, or 5.0 using acetate buffer. The size changes of these polymersomes under varied pH conditions were then tracked using DLS measurement at different time points.

Figure 5:
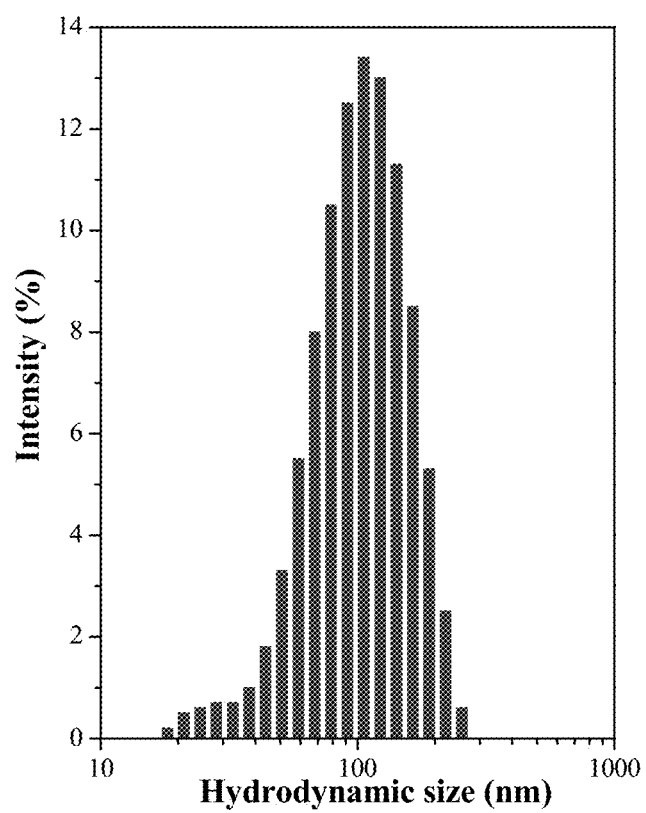
FIG. 5 is a bar graph of light intensity vs. hydrodynamic size of crosslinked PEG-Fu-DiTT polymersomes.
Figure 6A:
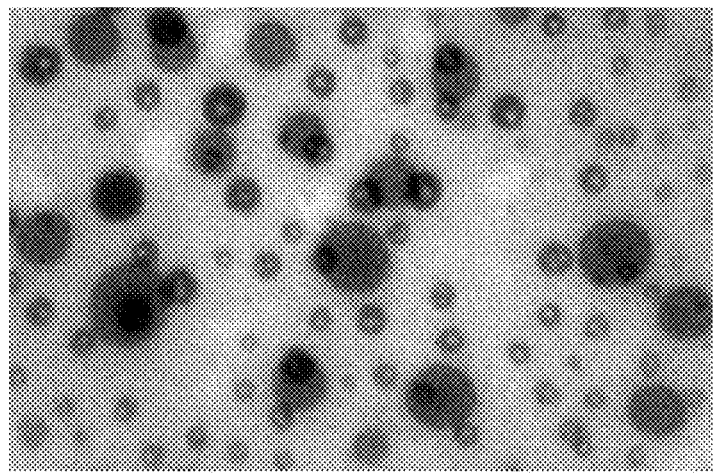
FIGS. 6A and 6B depict transmission electron microscope images of the crosslinked PEG-Fu-DiTT polymersomes.
Figure 6B:
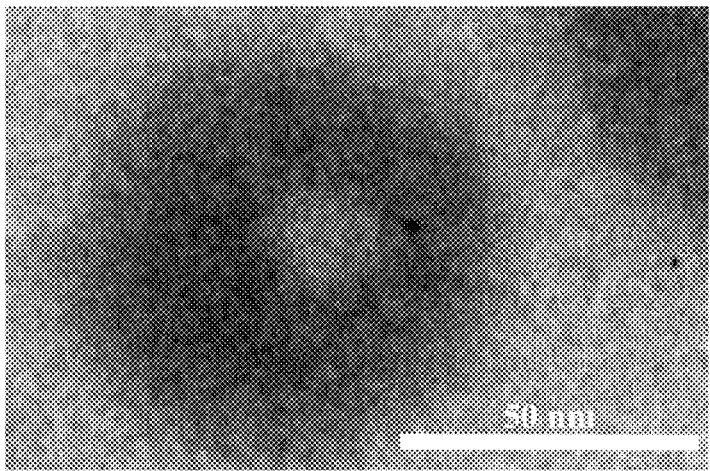

After chemical crosslinking, a decrease in both the polymersome size and PDI was detected by dynamic light scattering (DLS) with average diameters of 96.3±2.4 nm (FIG. 4). There was also a slight change in the surface zeta potential with average values of −2.8±1.1 mV for crosslinked polymersomes. FIG. 5 depicts the diameter of the crosslinked PEG-Fu-DiTT polymersomes as a function of light intensity, showing a maximum diameter of approximately 100 nm at 14% intensity. FIGS. 6A and 6B show transmission electron microscopy (TEM) images at different magnifications, showing a size of approximately 100 nm, which is consistent with the sizes determined from DLS. In addition, the TEM images demonstrated a void configuration for PEG-Fu-DiTT, wherein the dark edge in FIG. 6B represents the shell of the polymersome while the central white region indicates the hollow core of the polymersome.

Figure 13A:
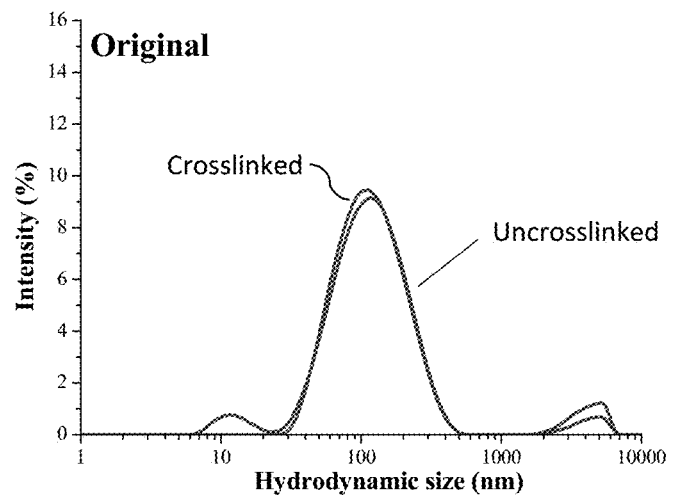
FIGS. 13A-D depict plots of intensity vs. hydrodynamic size of crosslinked and uncrosslinked PEG-Fu-DiTT polymersomes without additives, in the presence of fetal bovine serum, in the presence of sodium dodecyl sulfate, and in the presence of sodium chloride.
Figure 13B:
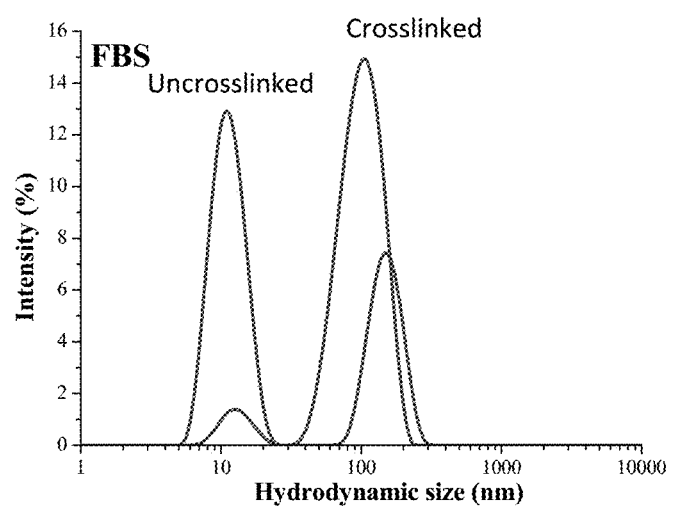
Figure 13C:
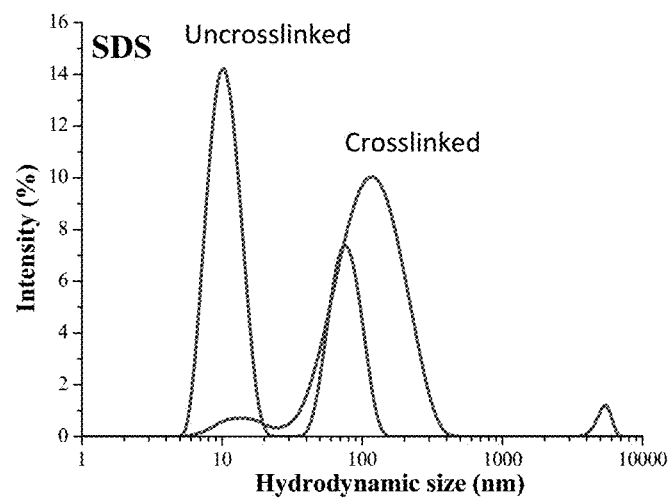
Figure 13D:
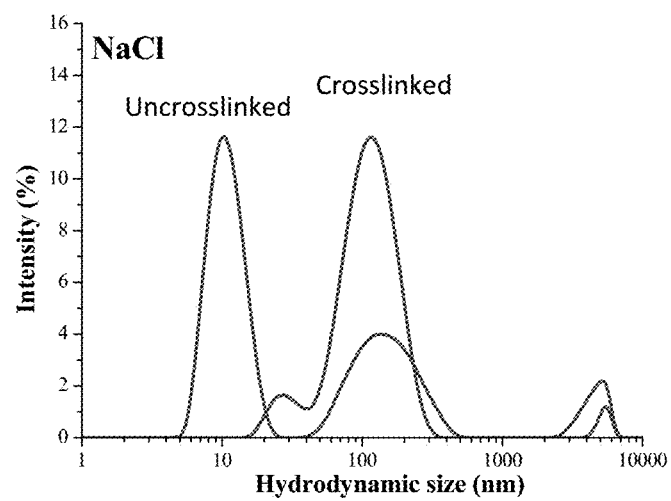

A stability test of PEG-Fu-DiTT polymersomes upon exposure to proteins, surfactants and salt ions was conducted using DLS. FIGS. 13A-13D show plots of intensity vs. hydrodynamic size without additives, in 10% fetal bovine serum (FBS), in 5 mM sodium dodecyl sulfate (SDS) solution, and in 0.9% NaCl solution, respectively. See FIGS. 13A-13D. FIGS. 13B-13D showed that the crosslinked polymersome kept a stable size in 10% FBS, 5 mM SDS and 0.9% NaCl solution. However, for uncrosslinked polymersomes, a large portion disassembled and formed a population of particles with size ~10 nm when exposed to these environmental changes. These results indicate that the polymersome gained enhanced stability after crosslinking of the inside chains, further supporting their utility as in vivo drug delivery vehicles.

Figure 7A:
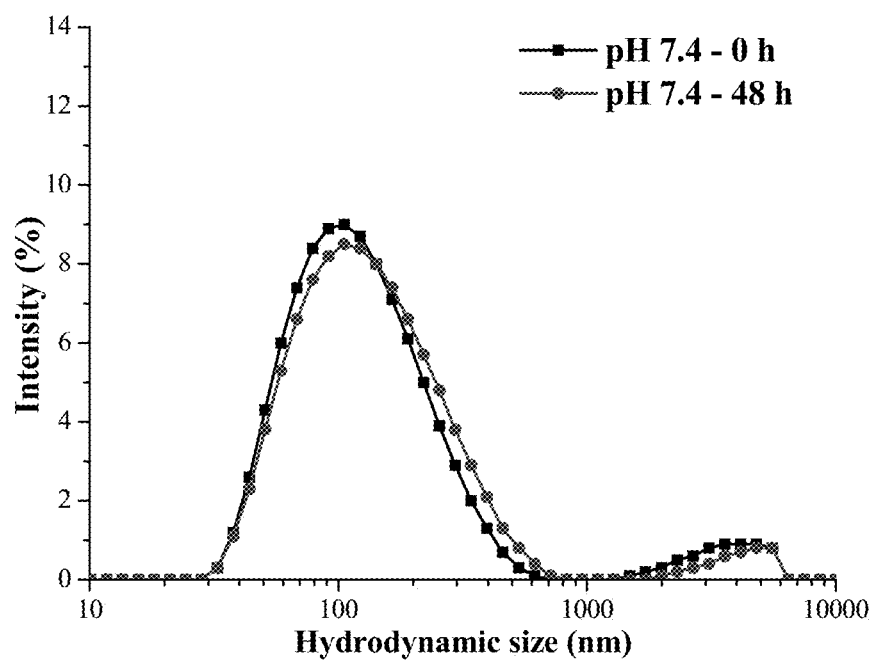
FIGS. 7A-B depict plots of intensity vs. hydrodynamic size of crosslinked PEG-Fu-DiTT polymersomes at pH 7.4 (FIG. 7A) and 5.0 (FIG. 7B) at various time points.
Figure 7B:
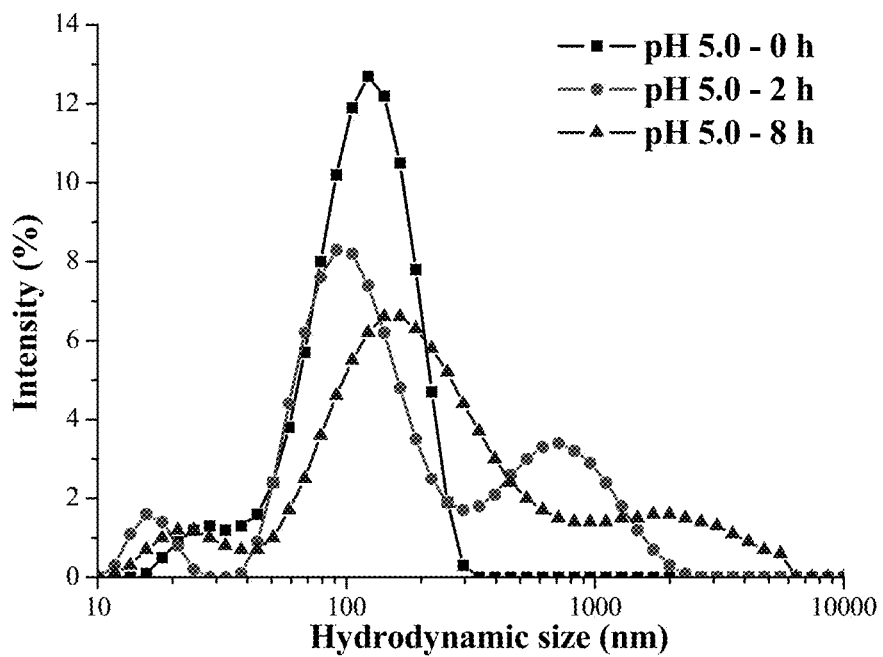

The size change of crosslinked PEG-Fu-DiTT polymersomes in response to pH changes was followed by DLS measurements. FIG. 7A is a plot of light intensity vs. hydrodynamic size at 0 hours of exposure to pH 7.4 conditions (squares) and at 48 hours of exposure (circles). The plots demonstrate little change in the size of crosslinked polymersomes, indicating a strong stability of crosslinked PEG-Fu-DiTT polymersomes under neutral environments. FIG. 7B is a plot of light intensity vs. hydrodynamic size at 0 hours of exposure to pH 5.0 conditions (squares), 2 hours of exposure to pH 5.0 conditions (circles), and 8 hours of exposure to pH 5 conditions (triangles). FIG. 7B demonstrated lower light intensity with increasing hydrodynamic size. Swelling as indicated by the appearance of a submicrometer/micrometer-sized particle peak after 2 hours of incubation in pH 5.0 solution was observed. With further increase of the incubation time to 8 hours, the majority of crosslinked polymersomes swelled, with the highest particle size peak shifting to 200 nm. In particular, a small portion of the polymersomes were detected to swell into the micrometer level. After 8 hours, no further changes in polymersome size were detected. This swelling effect is understood to be caused by hydrolysis of the PEG-Fu-DiTT acetal groups under low pH conditions to result in hydrophilic polymers that import water into the polymersome.

Example 4—Loading of Doxorubicin into Polymersomes

Doxorubicin-loaded (DOX-loaded) polymersomes were prepared by sequentially adding 400 µL of an aqueous solution of DOX.HCl (7.5 mg/mL) and 4 mL of a 0.3% PVA solution to 1 mL of PEG-Fu-DiTT copolymer dissolved in THF solvent (20 mg/mL) while stirring. Residual THF was removed by rotary evaporation. Crosslinked polymersomes were prepared by adding of 40 µL of 0.3 M ammonium persulfate (APS) and 40 µL of 0.3 M tetramethylethylenediamine (TEMED) to the polymersomes solution. The mixture was transferred to a dialysis tubing (Pierce, MWCO 2000) and dialyzed against phosphate buffer (10 mM, pH 7.4) for 12 hours in the dark, and the media was changed at least 3 times. The dialysis media was collected and the concentration of DOX in the media was quantified using a UV-vis absorbance microplate reader (SpectraMax Plus 384, Molecular Devices, Sunnyvale, Calif.). The detection wavelength was set at 490 nm and calibration curve was obtained with a series of DOX.HCl solutions of known concentrations. The drug loading content (DLC) and drug loading efficiency (DLE) of DOX encapsulated in polymersomes, respectively, were calculated according to the following formulas:

DLC (%)=[weight of drug loaded/weight of drug-loaded polymersomes)]×100%

DLE (%)=[weight of drug loaded/weight of drug in feed]×100%

DOX-loaded uncrosslinked and crosslinked polymersomes were determined to have hydrodynamic sizes of 113.9±4.6 nm and 103.5±5.3 nm, respectively, showing an increase in size with respect to the empty polymersomes due to encapsulation of DOX (FIG. 4). Zeta potential measurements detected values of −1.3±0.5 and −1.3±0.3 for uncrosslinked and crosslinked DOX loaded polymersomes, implying negative surface charges. The DLC and DLE of DOX in the crosslinked polymersomes were calculated to be 6.8% and 52.2%, respectively. These results indicate a successful loading of DOX into the polymersomes with a slightly enlarged size and negative surface charge.

Example 5—In Vitro Release Profile of DOX

The release profiles of DOX from PEG-Fu-DiTT polymersomes were investigated at pH 5.0 and pH 7.4 at 37° C. DOX-loaded polymersomes were prepared according to the process in Example 4 with a final polymer concentration of 5 mg/mL and then divided into two aliquots of 4 mL each. The pH was adjusted to pH 7.4 using phosphate buffer or to 5.0 using acetate buffer, then transferred to dialysis tubes with a molecular weight cut-off (MWCO) of 2000. Dialysis tubes were then immersed in corresponding pH 5.0 or pH 7.4 buffer (15 mL, 0.1 M) with constant shaking at 37° C. At certain time points, 1 mL of release medium was taken out for determination of the DOX concentration on a UV-vis absorbance microplate reader (490 nm), using calibration curves established by corresponding buffer solutions (pH 5.0 or pH 7.4) of known DOX.HCl concentrations. The release media was then replenished with equal volume of fresh buffer immediately. Each experiment was conducted in triplicate and average values were calculated with standard deviations.

Figure 8:
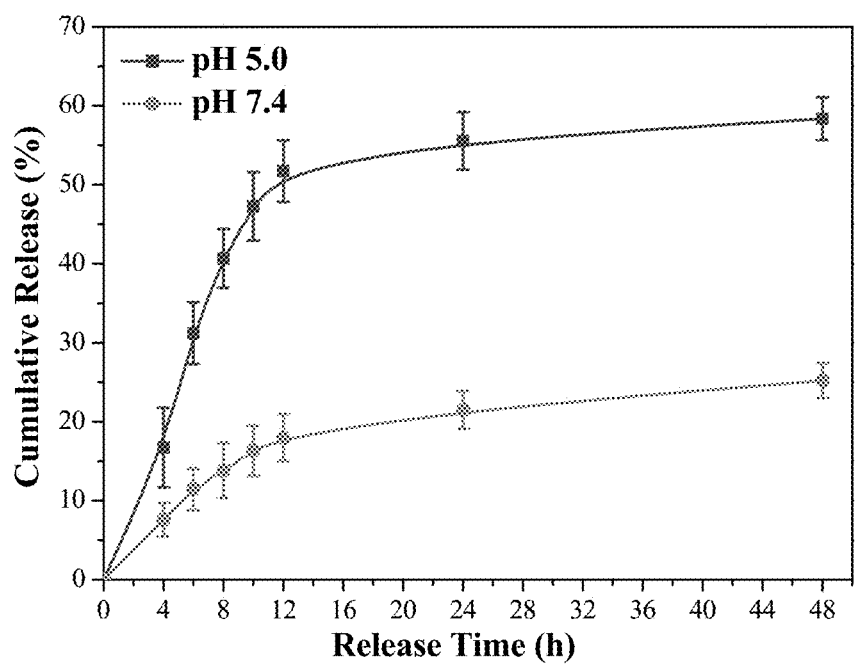
FIG. 8 depicts plots of cumulative release vs. release time of doxorubicin-containing polymersomes at pH 7.4 (circles) and 5.0 (squares).

Release of DOX from polymersomes under physiological (pH 7.4) or acidic conditions (pH 5.0, selected to mimic acidic conditions in lysosomes) was investigated. FIG. 8 shows plots of DOX release from polymersomes as a function of time at pH 5.0 (top plot) and pH 7.4 (bottom plot). A substantially higher DOX content in acidic release medium (pH 5.0) than in physiological conditions (pH 7.4) over a period of 48 h was observed. DOX-loaded polymersome (DOX-PS) demonstrated good stabilities in physiological conditions, and a DOX amount of 21.5±2.4% and 25.2±2.2% were released after incubation in the release medium for 24 h and 48 h, respectively. However, under the acidic medium, DOX release was much faster and the release amount increased to 55.6±3.7% and 58.4±2.7% at 24 h and 48 h, respectively. Not wishing to be bound by theory, this rapid DOX release is believed to be largely due to the polymersome expansion caused by hydrophobic to hydrophilic transformation of PEG-Fu-DiTT polymer chains through acetal hydrolysis, consistent with the size swelling trend shown for unloaded polymersomes in FIG. 6B. These results collectively show that pH-sensitive degradable polymersomes based on PEG-Fu-DiTT polymers are able to efficiently load and rapidly release DOX in a low pH environment in endosomes and lysosomes, which renders them particularly appealing for the delivery of hydrophilic anticancer drugs.

Example 6—Cell Viability

HeLa cells were used as a model cancer cell for cytotoxicity evaluation. Trypsinized HeLa cells were seeded onto 48-well tissue culture polystyrene (TCPS) plates at 10,000 cells cm$^{-2}$. Cells were then cultured in Dulbecco's Modified Eagle's Medium (DMEM) supplemented with FBS, 100 U/mL penicillin, 2 mM L-glutamine, and 0.1 mg/mL streptomycin for 24 h to allow adhesion. To evaluate the cytotoxicity of PEG-Fu-DiTT polymersomes, empty samples without loaded drugs were prepared, dialyzed against phosphate-buffered saline (PBS) for 2 days, and lyophilized for 3 days. The dried polymersomes were then incubated with HeLa cells at concentrations of 0.1, 0.5, 1.0 and 2.0 mg/mL for 3 days. Wells seeded with the same HeLa cell density but without added polymersomes were used as positive controls. The relative cell densities in each group were determined by MTS assay (CellTiter 96 Aqueous One Solution, Promega, Madison, Wis.) by comparing the optical density (OD) value to that of positive controls (which were set at 100% cell density). To evaluate the cancer killing effect, similar cell culture procedures were used by adding DOX-loaded polymersomes or free drugs at concentrations of 0.01, 0.1, 0.5, 1, 5, 10 and 50 μg/mL.

Figure 9:
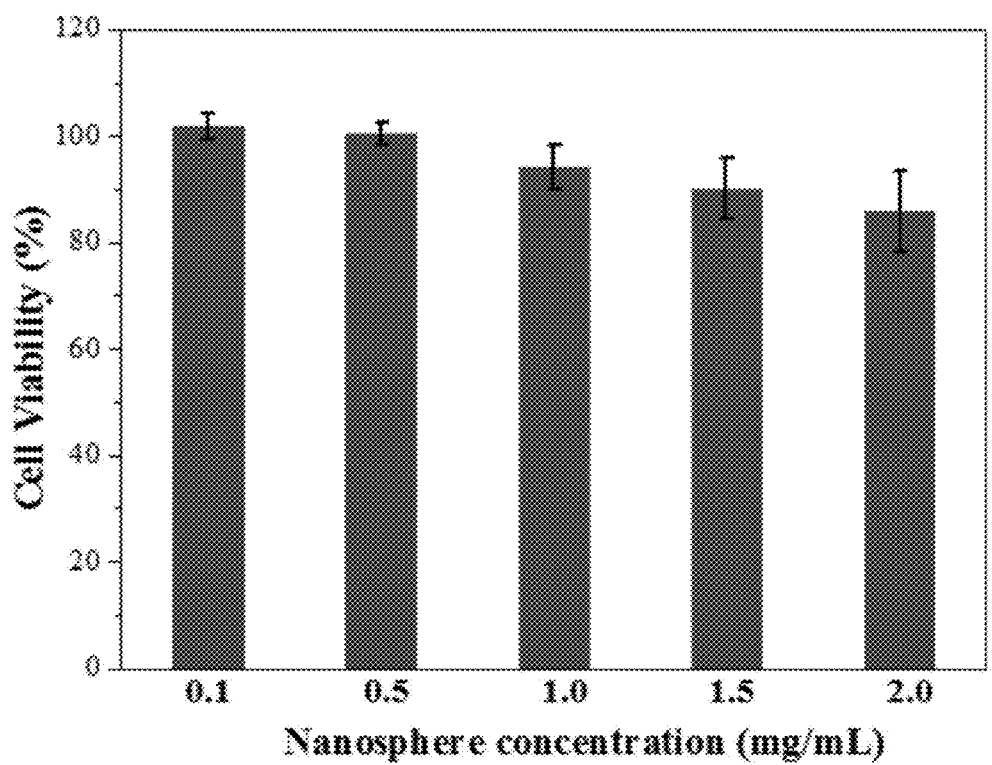
FIG. 9 is a bar graph of cell viability vs. nanosphere concentration of empty PEG-Fu-DiTT polymersomes.
Figure 10:
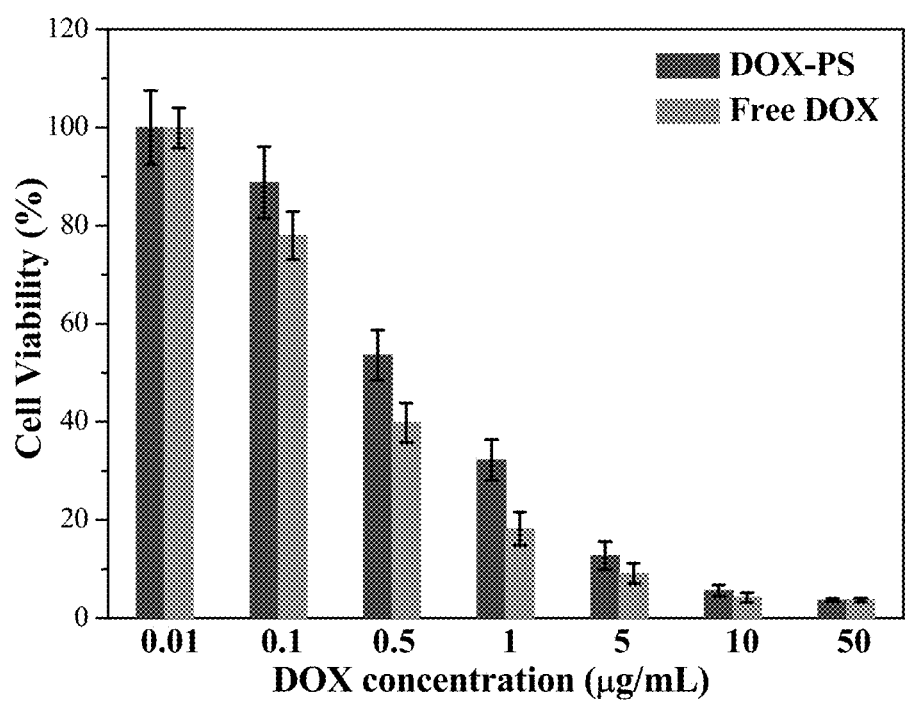
FIG. 10 is a bar graph of cell viability vs. nanosphere concentration of doxorubicin-containing polymersomes (left-hand bars) and free doxorubicin (right-hand bars).

FIG. 9 is a bar graph depicting cell viability at increasing nanosphere concentrations of empty polymersomes prior to loading of DOX.HCl, showing good biocompatibility with HeLa cells. FIG. 10 is a bar graph depicting cell viability at increasing nanosphere concentrations of polymersome-encapsulated DOX (DOX-PS, left set of bars) and unencapsulated DOX (right set of bars), showing an inhibition effect toward cancer cells even at a low concentration of 10 μg/mL. As demonstrated in FIG. 10, under the same concentration of DOX.HCl administration for 3 days, DOX-PS demonstrated an excellent killing effect comparable to that of the unencapsulated drug.

Example 7—Cellular Uptake of Polymersomes

HeLa cells were co-cultured with DOX-loaded polymersomes in DMEM at a drug concentration of 10 μg/mL, as described in Example 6. At time points of 1, 2, 4 hours, the culture medium was removed and cells were washed with PBS three times and then fixed in 4% paraformaldehyde. After 10 min, paraformaldehyde was removed and cells were washed three times with PBS then stained with DAPI (4',6-diamidino-2-phenylindole) for 2 min. DOX fluorescence from polymersomes and DAPI fluorescence from cellular nuclei were visualized and photographed by Axiovert 25 Zeiss light microscope. DOX fluorescence from polymersomes appeared red, and DAPI fluorescence from cellular nuclei appeared blue.

Figure 11:
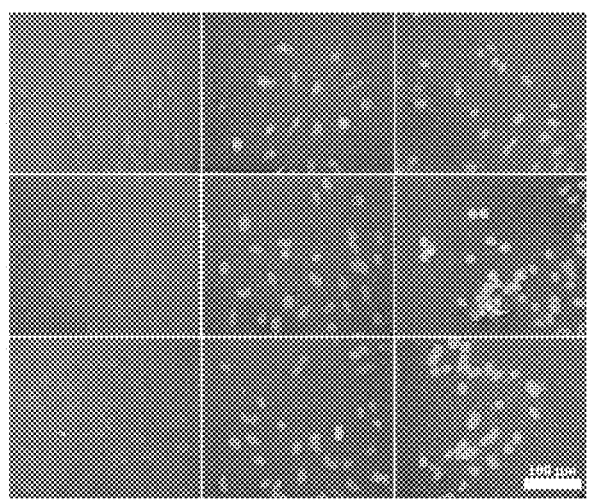
FIG. 11 depicts fluorescence images of HeLA cells with and without doxorubicin.

Cellular uptake of DOX-PS particles were investigated through imaging of DOX fluorescence after 1, 3 and 5 hours of co-culture with HeLa cells. FIG. 11 shows a grid of fluorescent images, with the first column showing the positive controls, the second column showing cells incubated with free DOX, and the third column showing cells incubated with DOX-PS. The first, second, and third rows correspond to incubation times of 1, 3, and 5 hours respectively. All of the positive control groups without drug administration showed no DOX fluorescence. Cells with free DOX.HCl demonstrated red fluorescence after 1 h incubation, with a slight increase in intensity at 3 and 5 hour time points. HeLa cells with DOX-PS exhibited similar DOX fluorescence at 1 hour. However, the fluorescence intensified at 3 hour and 5 hour time points.

Figure 12A:
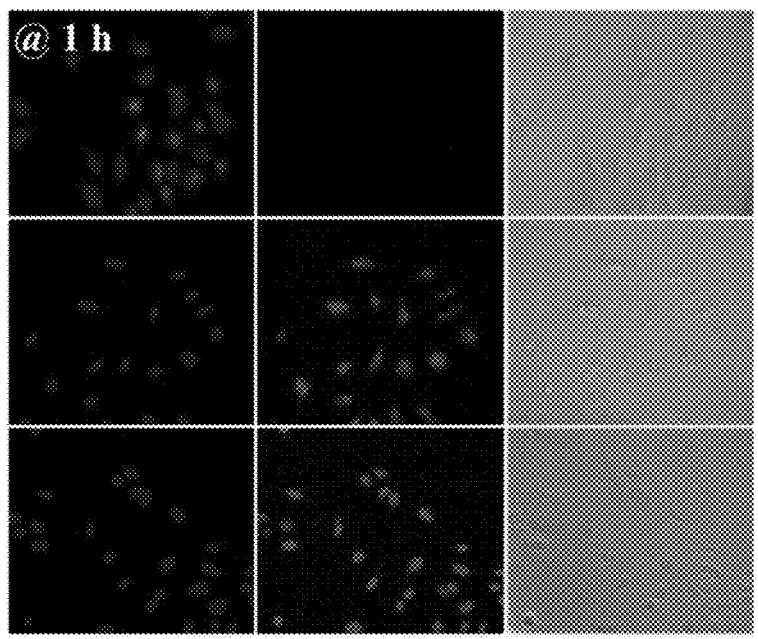
FIGS. 12A-C depict fluorescence images of HeLA cells at 1 hour, 3 hours, and 5 hours of incubation with and without doxorubicin.
Figure 12B:
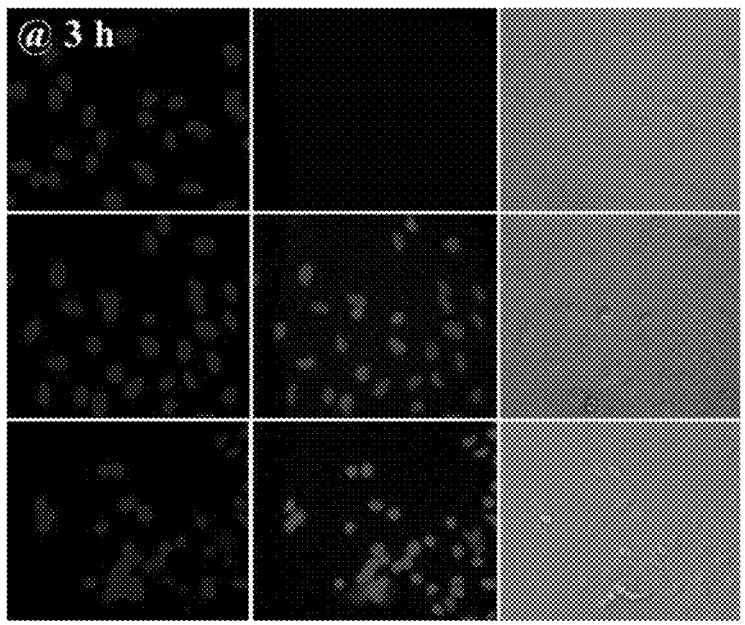
Figure 12C:
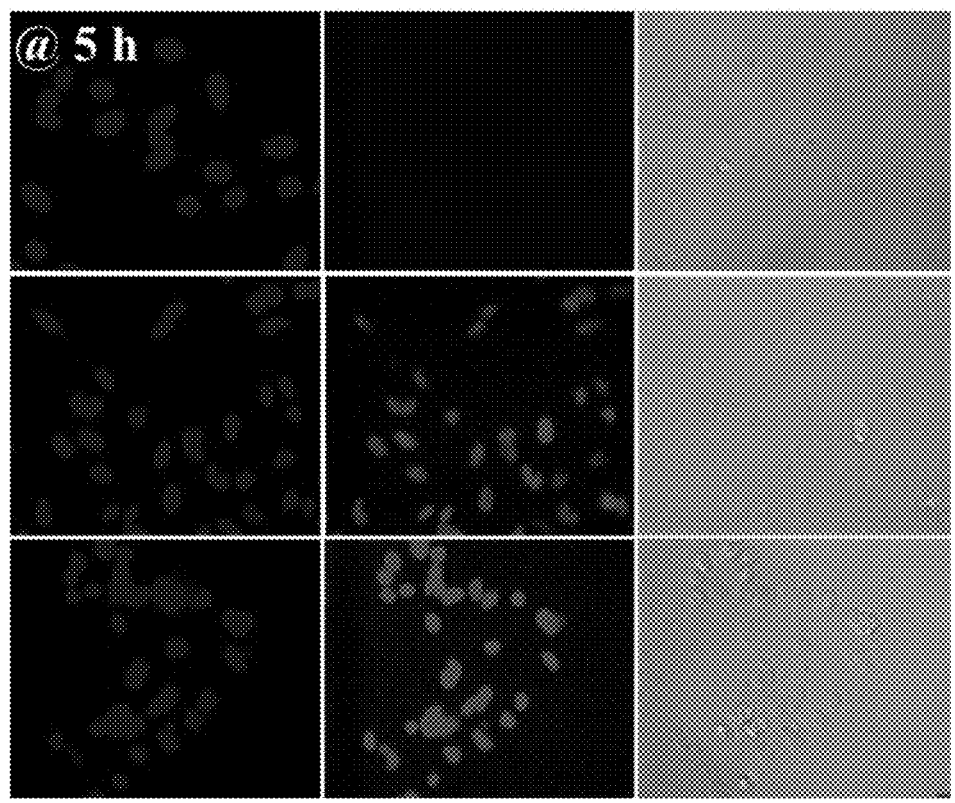

FIGS. 12A-12C depict grids of fluorescence images taken at 1 hour of incubation, 3 hours of incubation, and 5 hours of incubation, respectively. For each of FIGS. 12A-12C, the first column corresponds to DAPI fluorescence, the second column corresponds to DOX fluorescence, and the third column corresponds to light illumination; while the first row of images are the control cells, the second row the cells incubated with free DOX, and the third row the cells incubated with DOX-PS. Cells were observed to contract and detach from culture plates at 3 hours (FIG. 12B) and 5 hours (FIG. 12C) with incubation of DOX-PS. It is believed that the cellular uptake of large particles is generally achieved by endocytosis. After endocytosis, particles encounter an acidic environment in intracellular organelles (e.g., endosomes or lysosomes). This acidic environment is believed to cause rapid acetal hydrolysis of the PEG-Fu-DiTT polymersomes, which further result in immediate DOX release and robust cancer-killing effects, as evidenced by cell contraction and low cancer cell viability.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A polymer of Formula (I):

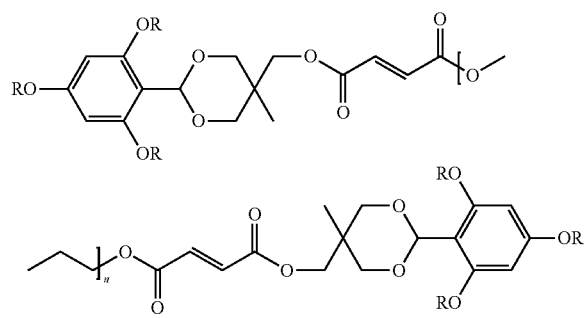

wherein:
each R is independently C1-6 alkyl; and
n is an integer between 1 and 50.
2. The polymer of claim 1, wherein n is an integer between 10 and 30.
3. The polymer of claim 2, wherein n is an integer between 15 and 25.
4. The polymer of claim 3, wherein n is 20.
5. The polymer of claim 1, wherein each R is methyl.
6. A polymersome comprising a polymer of Formula (I):

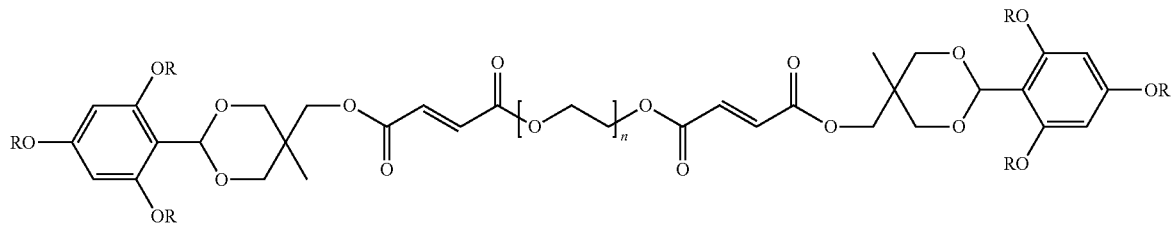

wherein:
each R is independently C1-6 alkyl;
n is an integer between 1 and 50.
7. The polymersome of claim 6, wherein the polymer of Formula (I) is crosslinked.
8. The polymersome of claim 6, wherein the polymersome further comprises a therapeutic agent.
9. The polymersome of claim 6, wherein the polymersome further comprises a hydrophilic anticancer agent.
10. The polymersome of claim 9, wherein the hydrophilic anticancer agent is selected from the group consisting of doxorubicin, paclitaxel, 5-fluoroucacil, 6-mercaptopurine, cyclophosphamide, bleomycin, daunorubicin, epirubicin, methotrexate, vinblastine, homoharringtonine, actinomycin-D, mitocycin-c, and etoposide.
11. The polymersome of claim 10, wherein the hydrophilic anticancer agent is doxorubicin.
12. The polymersome of claim 6, wherein n is an integer between 10 and 30.
13. The polymersome of claim 12, wherein n is an integer between 15 and 25.
14. The polymersome of claim 13, wherein n is 20.
15. The polymersome of claim 6, wherein each R is methyl.
16. The polymersome of claim 6, wherein the diameter of the polymersome is about 50 to about 150 nm.
17. The polymersome of claim 16, wherein the average diameter of the polymersome is about 90 to about 120 nm.
18. A pharmaceutical composition comprising a polymersome of claim 6, and a pharmaceutically acceptable excipient.
19. A method of treating cancer in a patient, the method comprising administering to the patient a therapeutically effective amount of a polymersome of claim 6.
20. A method for administering a therapeutic agent to a patient in need thereof, the method comprising administering to the patient a polymersome of claim 6.

* * * * *

UNITED STATES PATENT AND TRADEMARK OFFICE
CERTIFICATE OF CORRECTION

PATENT NO. : 10,188,606 B2
APPLICATION NO. : 15/728181
DATED : January 29, 2019
INVENTOR(S) : Xifeng Liu, Michael J. Yaszemski and Lichun Lu Page 1 of 1

It is certified that error appears in the above-identified patent and that said Letters Patent is hereby corrected as shown below:

On the Title Page

Column 2 (Other Publications), Line 4, delete "4(4):" and insert -- 6(4): --, therefor.

Column 2 (Other Publications), Line 5, delete ""Expansible" and insert -- "Expansile --, therefor.

Column 2 (Other Publications), Line 7, delete "Polymersome" and insert -- Polymersomes --, therefor.

Column 2 (Other Publications), Line 8, delete "Robus" and insert -- Robust --, therefor.

In the Claims

Column 17, Line 64, Claim 1, delete "C1-6 alkyl;" and insert -- $C_{1-6}$ alkyl; --, therefor.

Column 18, Line 20 (approx.), Claim 6, delete "C1-6 alkyl;" and insert -- $C_{1-6}$ alkyl; --, therefor.

Column 18, Line 20 (approx.), Claim 10, delete "5-fluoroucacil," and insert -- 5-fluorouracil, --, therefor.

Column 18, Line 36 (approx.), Claim 10, delete "mitocycin-c," and insert -- mitomycin-c, --, therefor.

Signed and Sealed this
Twenty-third Day of June, 2020

Andrei Iancu
*Director of the United States Patent and Trademark Office*